United States Patent
Durfee et al.

(10) Patent No.: US 6,891,619 B2
(45) Date of Patent: May 10, 2005

(54) FLAME TREATED TURBIDITY SENSOR

(75) Inventors: Anthony L. Durfee, Jackson, TN (US); John H. Miilu, Jackson, TN (US)

(73) Assignee: Maytag Corporation, Newton, IA (US)

( * ) Notice: Subject to any disclaimer, the term of this patent is extended or adjusted under 35 U.S.C. 154(b) by 278 days.

(21) Appl. No.: 10/126,405

(22) Filed: Apr. 19, 2002

(65) Prior Publication Data

US 2003/0197868 A1 Oct. 23, 2003

(51) Int. Cl.$^7$ .............................................. G01N 21/59
(52) U.S. Cl. ................................. 356/442; 138/57 D
(58) Field of Search ............................... 356/339, 442; 138/57 D

(56) References Cited

U.S. PATENT DOCUMENTS

| | | | | |
|---|---|---|---|---|
| 3,889,000 A | * | 6/1975 | Cante et al. .................. 426/84 |
| 4,740,287 A | * | 4/1988 | Cawlfield .................... 204/258 |
| 5,041,266 A | * | 8/1991 | Fox ............................. 422/102 |
| 5,331,177 A | * | 7/1994 | Kubisiak et al. ............. 250/574 |
| 5,355,048 A | * | 10/1994 | Estes ........................... 310/334 |
| 5,589,935 A | * | 12/1996 | Biard .......................... 356/339 |
| RE35,566 E | * | 7/1997 | Boyer et al. .................. 356/72 |
| 6,206,841 B1 | * | 3/2001 | Cunningham et al. ...... 600/584 |
| 6,468,076 B2 | * | 10/2002 | Kawamura ................... 433/29 |

FOREIGN PATENT DOCUMENTS

JP        60151919        1/1987

OTHER PUBLICATIONS

Yosha (*Journal of Japan Thermal Spraying Society*), "Fundamental Study on Development of Wet Optical Sensor by the Thermal Spraying", vol. 33, No. 4, pp. 40–48, Dec. 1996.

* cited by examiner

Primary Examiner—Richard A. Rosenberger
(74) Attorney, Agent, or Firm—McKee, Voorhees & Sease

(57) ABSTRACT

An improved turbidity sensor is provided with a pair of spaced apart arms respectively housing a light transmitter and a light receiver, with the receiver adapted to sense the light from the transmitter and generate a corresponding output signal. The opposing surfaces of the arms adjacent the transmitter and receiver are flame treated for approximately one second each so as to raise the surface energy such that bubble-induced noise is reduced or eliminated for a more accurate output signal.

16 Claims, 2 Drawing Sheets

FLAME TREATED TURBIDITY SENSOR

BACKGROUND OF THE INVENTION

Turbidity sensors are commonly used in dishwashers to sense the amount of food particles in the water. The sensors typically are submerged in the water from the wash chamber. The wash water is recirculated during the wash operation until it reaches a predetermined level of turbidity wherein the food particles exceed a desired level. This dirty water is then discharged and replaced with fresh, clean water.

The turbidity sensors typically include an infrared transmitter and an infrared receiver or sensor mounted in a plastic housing. A problem associated with convention turbidity sensors is the accuracy of the output signal. The housing has a tendency to accumulate small bubbles while the water flows over the housing. When the bubbles collect on or travel over the area of the housing through which the infrared signal is traveling, the output signal of the sensor is adversely affected by this bubble-induced noise.

There have been various attempts to minimize or eliminate the problems associated with bubbles on the turbidity sensor housing, though none of the solutions have proved sufficiently effective. These prior art efforts include increasing the water fill level to reduce bubbles in the water; increasing the water velocity; turning the sensor 90° relative to the water flow; adding baffles in the water flow to change the turbulence thereof; polishing the surface of the sensor with a compound; using hot air to re-flow and smooth the surface; and coating the sensor with super glue.

Accordingly, a primary objective of the present invention is the provision of an improved turbidity sensor which is flame treated to reduce the adverse bubble effect on the sensor output.

Another objective of the present invention is the provision of a method of manufacturing a turbidity sensor wherein the housing of the sensor is treated to affect the surface energy of the housing.

A further objective of the present invention is the provision of a method of manufacturing a turbidity sensor wherein the plastic housing is subjected to a single and rapid application of heat to the surface during the manufacturing process.

A further objective of the present invention is the provision of an improved turbidity sensor having a reduction in bubble-induced noise in the output signal of the turbidity sensor.

Another objective of the present invention is the provision of an improved turbidity sensor which is economical to manufacture and accurate in use.

These and other objectives will be apparent from the following description of the invention.

SUMMARY OF THE INVENTION

The improved turbidity sensor of the present invention includes a molded plastic housing have two upstanding arms with an infrared transmitter in one arm and an infrared receiver in the other arm. The arms are spaced apart such that wash water flows between the arms. The strength of the infrared signal from the transmitter is sensed by the receiver, which generates an output signal depending upon the turbidity of the water, through which the infrared light passes between the upstanding arms. The opposing surfaces of the housing of the upstanding arms is flame treated in a single and rapid application so as to affect the surface energy of the plastic adjacent the transmitter and receiver, thereby reducing the bubble-induced noise in the sensor's output signal. In the manufacture of the sensor, the plastic housing is molded and heat treated with a propane flame directed at approximately a 30° angle with respect to the housing surfaces adjacent the IR transmitter and receiver at a distance of approximately 40 millimeters for a period of approximately one second on each surface.

DETAILED DESCRIPTION OF THE INVENTION

Figure 1:
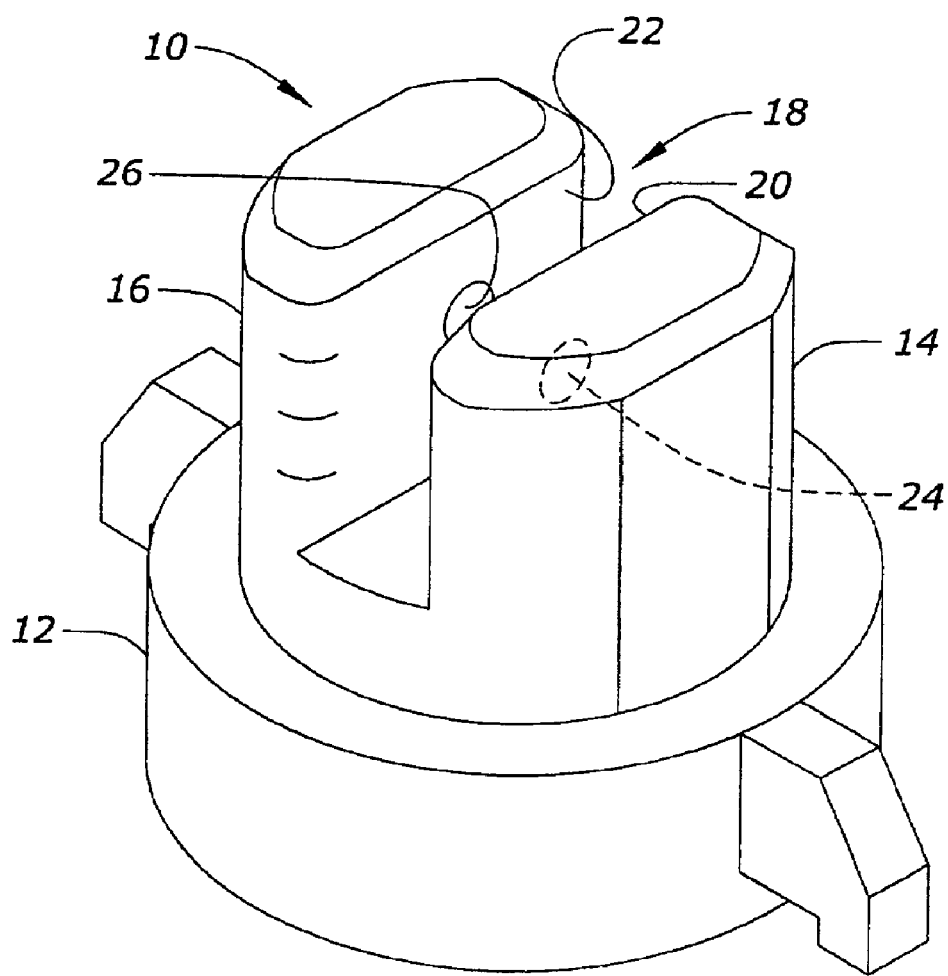
FIG. 1 is a perspective view of the turbidity sensor of the present invention.
Figure 2:
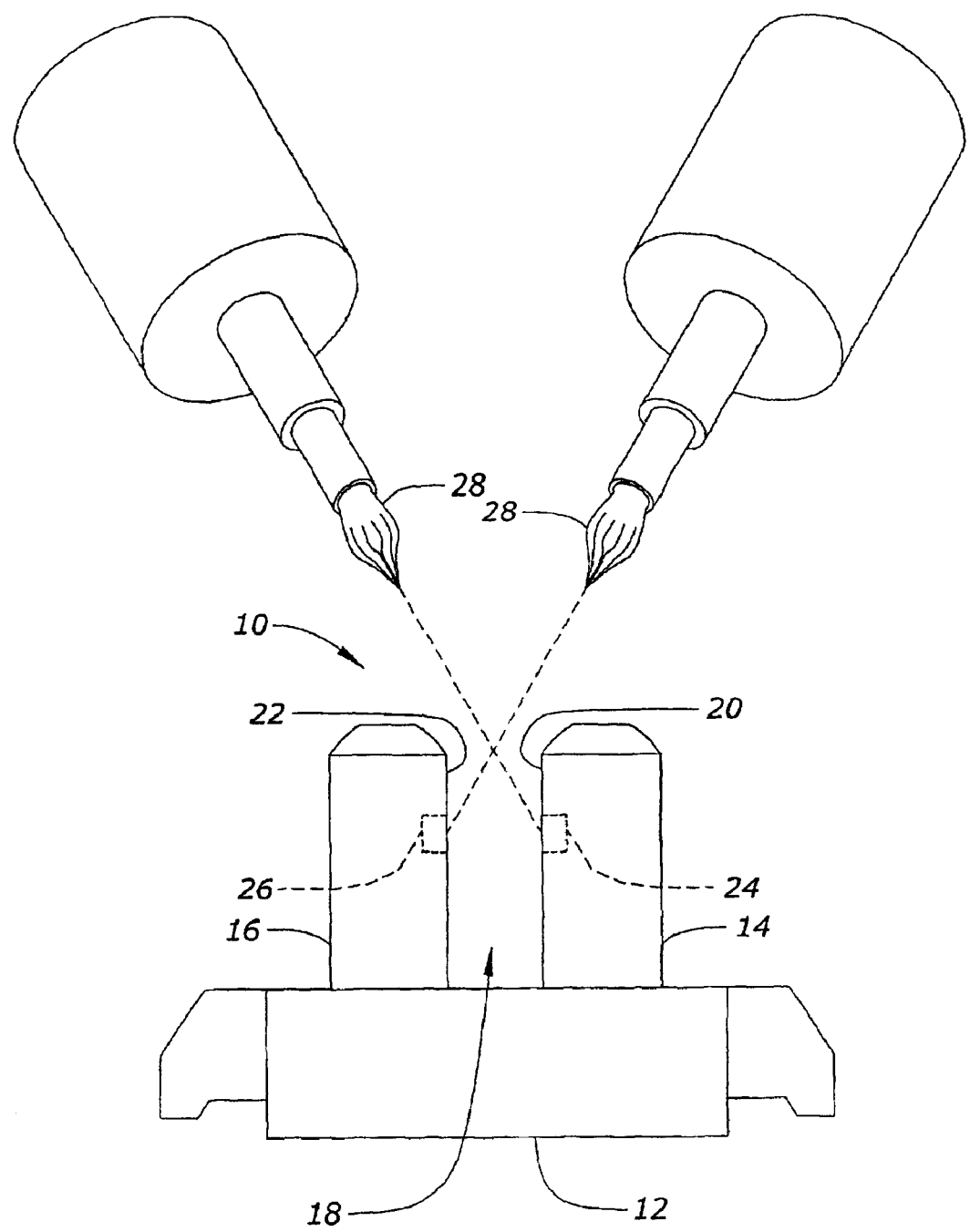
FIG. 2 is an end elevation view of the sensor showing the application of the flame to the inner housing surfaces adjacent the IR receiver and transmitter.

The turbidity sensor of the present invention is generally designated by the reference numeral 10 in the drawings. The sensor typically is mounted in the water of the washing chamber of a dishwasher. This location is conventional.

The turbidity sensor 10 includes a base 12 and a pair of upstanding arms 14, 16. The arms are spaced apart from one another so as to define a gap 18 therebetween. The arms 14, 16, thus have opposing inner surfaces 20, 22, respectively.

The arm 14 houses an infrared transmitter 24, while the arm 16 houses an infrared receiver 26. The transmitter 24 and receiver 26 are opposite one another, such that the receiver 26 senses the infrared light emitted by the transmitter 24, and outputs a signal corresponding to the strength of the infrared light. The strength of the IR light varies, depending on the turbidity of the wash water passing between the arms 14, 16. When the water is clean, more IR light is sensed, such that the receiver 26 generates an increased voltage output. When the wash water becomes dirty, less IR light is sensed, such that the receiver 26 generates a lower voltage output. The level of the voltage output determines whether the water is recycled or drained from the washing machine.

In order to minimize or reduce the bubble-induced noise in the output signal of the turbidity sensor 10, the inner surfaces 20, 22 are heat treated so as to affect the surface energy. Preferably, the heat treatment is performed during the manufacture process of the turbidity sensor, after molding of the plastic housing which forms the arms 14, 16. The heat is preferably generated by a propane flame 28 which is directed at an angle of approximately 30° to each surface from a distance of approximately 40 millimeters. Preferably, the flame treatment is a single and rapid step, lasting approximately one second for each surface 20–22. In tests, the inner surfaces 20, 22 of the arms 14, 16 had a surface energy of 22 mN/m (milli-Newtons per meter) after molding. After flame treatment, the surfaces 20, 22 had a surface energy of 64 mN/m. Thus, the surface energy increased approximately three times for the one second flame treatment. The temperature of the flame is estimated to be 1400° F.±200° F.

As a result of the flame treatment, the surfaces 20, 22 of the arms 14, 16 are more completely wetted, without bonding of air bubbles thereto, which otherwise generate bubble induced noise which adversely effects the output signal of the sensor. Without the adverse bubble effect, the output signal of the sensor 10 is more accurate.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A method of manufacturing a turbidity sensor, comprising:

molding a plastic housing;

installing a sensor in the housing to generate an output signal corresponding to water turbidity;

heat treating the housing to affect the surface energy of the housing so the sensor avoids bubble-induced noise; and the heat being applied for a period ranging between 0.5 and 4 seconds.

2. The method of claim 1, wherein the heat treatment is the application of a flame.

3. The method of claim 1 wherein the heat temperature ranges between 1400° F.±200° F.

4. The method of claim 1 wherein the heat treatment is the application of a propane flame for approximately one second.

5. The method of claim 1 wherein the heat treatment is performed in a single step.

6. The method of claim 1 wherein the surface energy is increased at least 100%.

7. The method of claim 1 wherein the surface energy is approximately three times greater after the heat treatment than before the heat treatment.

8. The method of claim 1 wherein the surface energy is approximately 64 mN/m after treatment.

9. A method of manufacturing a turbidity sensor, comprising:

molding a plastic housing;

installing a sensor in the housing to generate an output signal corresponding to water turbidity;

heat treating the housing to affect the surface energy of the housing so the sensor avoids bubble-induced noise; and the heat temperature ranging between 1400° F.±200° F.

10. The method of claim 9 wherein the heat treatment is the application of a flame.

11. The method of claim 9 wherein the heat is applied for a period ranging between 0.5 and 4 seconds.

12. The method of claim 9 wherein the heat treatment is the application of a propane flame for approximately one second.

13. The method of claim 9 wherein the heat treatment is preformed in a single step.

14. The method of claim 9 wherein the surface energy is increased at least 100%.

15. The method of claim 9 wherein the surface energy is approximately three times greater after the heat treatment than before the heat treatment.

16. The method of claim 9 wherein the surface energy is approximately 64 mN/m after treatment.

* * * * *